(12) United States Patent
Cooper et al.

(10) Patent No.: US 10,722,535 B2
(45) Date of Patent: Jul. 28, 2020

(54) COMPOSITIONS DERIVED FROM COHN FRACTION PASTE AND USE THEREOF

(71) Applicant: KAMADA LTD., Ness Ziona (IL)

(72) Inventors: Ayelet Cooper, Rehovot (IL); Nachum Yonah, Gedera (IL); Liliana Bar, Rehovot (IL)

(73) Assignee: KAMADA LTD., Ness Ziona (IL)

( * ) Notice: Subject to any disclaimer, the term of this patent is extended or adjusted under 35 U.S.C. 154(b) by 47 days.

(21) Appl. No.: 15/752,193

(22) PCT Filed: Aug. 11, 2016

(86) PCT No.: PCT/IL2016/050875
§ 371 (c)(1),
(2) Date: Feb. 12, 2018

(87) PCT Pub. No.: WO2017/025965
PCT Pub. Date: Feb. 16, 2017

(65) Prior Publication Data
US 2018/0353543 A1 Dec. 13, 2018

Related U.S. Application Data

(60) Provisional application No. 62/204,482, filed on Aug. 13, 2015.

(51) Int. Cl.
| | |
|---|---|
| *A61K 38/00* | (2006.01) |
| *A61K 35/16* | (2015.01) |
| *A61K 38/38* | (2006.01) |
| *A61K 38/40* | (2006.01) |
| *A61K 38/01* | (2006.01) |
| *A61K 38/48* | (2006.01) |
| *A61K 9/00* | (2006.01) |
| *A61K 8/66* | (2006.01) |
| *A61K 8/98* | (2006.01) |
| *A61L 26/00* | (2006.01) |
| *A61Q 19/00* | (2006.01) |
| *A61K 38/44* | (2006.01) |
| *A61Q 19/08* | (2006.01) |
| *A61K 8/64* | (2006.01) |
| *C07K 16/06* | (2006.01) |
| *A61P 17/02* | (2006.01) |

(52) U.S. Cl.
CPC ............... *A61K 35/16* (2013.01); *A61K 8/64* (2013.01); *A61K 8/66* (2013.01); *A61K 8/983* (2013.01); *A61K 9/00* (2013.01); *A61K 9/0014* (2013.01); *A61K 38/014* (2013.01); *A61K 38/38* (2013.01); *A61K 38/40* (2013.01); *A61K 38/44* (2013.01); *A61K 38/4833* (2013.01); *A61L 26/0047* (2013.01); *A61P 17/02* (2018.01); *A61Q 19/00* (2013.01); *A61Q 19/08* (2013.01); *C07K 16/065* (2013.01); *C12Y 116/03001* (2013.01)

(58) Field of Classification Search
None
See application file for complete search history.

(56) References Cited

U.S. PATENT DOCUMENTS

| | | | | |
|---|---|---|---|---|
| 5,505,945 | A * | 4/1996 | Gristina | A61K 39/44 424/164.1 |
| 2003/0211137 | A1* | 11/2003 | Sierra | A61L 24/0026 424/445 |
| 2007/0065415 | A1* | 3/2007 | Kleinsek | A61K 35/12 424/93.7 |

FOREIGN PATENT DOCUMENTS

| | | |
|---|---|---|
| CN | 102977180 A | 3/2013 |
| WO | 2013/126904 A1 | 8/2013 |

OTHER PUBLICATIONS

Ascione, E., et al., "A Simple Method for Large-Scale Purification of Plasma-Derived Apotranferrin." Biotechnology and Applied Biochemistry, vol. 57.3, pp. 87-95 (2010).
International Search Report of PCT/IL2016/050875 dated Nov. 27, 2016.
Written Opinion of PCT/IL2016/050875 dated Nov. 27, 2016.

* cited by examiner

*Primary Examiner* — Jeanette M Lieb
(74) *Attorney, Agent, or Firm* — Polsinelli PC; Ron Galant

(57) ABSTRACT

The present invention provides compositions and methods for improving wound healing, reducing scar formation and/or promoting skin health and aesthetic appearance. In particular, the present invention provides protein compositions that are derived from Cohn fraction IV and/or IV-1 useful in promoting wound healing and for cosmetic care of the skin.

10 Claims, 6 Drawing Sheets

COMPOSITIONS DERIVED FROM COHN FRACTION PASTE AND USE THEREOF

FIELD OF THE INVENTION

The present invention relates to high value human plasma-derived protein compositions useful in therapeutics and cosmetics, particularly to compositions comprising a combination of proteins derived from Cohn fraction IV and/or Cohn fraction IV-1 paste useful for treating wounds and for skin care.

BACKGROUND OF THE INVENTION

Human blood plasma contains proteins serving many different functions including transport of lipids, hormones, vitamins and minerals in the circulatory system, regulation of acellular activity and functioning of the immune system and further function as enzymes, complement components, protease inhibitors and more.

Cohn fractionation process, initially developed by Edwin Joseph Cohn, is a process that includes series of purification steps which was originally developed for extracting albumin from blood plasma. Later the process was modified to purify other plasma proteins such as immunoglobulins, coagulation factors, and Alpha-1 Antitrypsin (AAT), also known as alpha-1 proteinase inhibitor. Variety of plasma ingredients are removed during the purification of this desired plasma proteins, usually regarded to as byproducts or waste.

The Cohn fractionation process includes elevation of ethanol concentration and pH decrease from the natural pH to a more acidic pH (around 4.8) and temperature decrease from room temperature to about (–)5° C. Five major fractions are precipitated during the process, with Fractions I, II, and III precipitating out at earlier stages and fractions IV, IV-1 and V each being an end product. Relatively to plasma composition, Fraction IV and Fraction IV-1 are enriched with relatively low molecular weight plasma proteins (<200 kD) including proteases, protease inhibitors and growth factors.

There is a tangible need for a large variety of skin care products for various cosmetic or medical purposes. For instance, skin care may be directed to avoiding or repairing skin damage as a result of one or more of various factors. Common examples of such factors are exposure to heat (which may result in burns), cold, drought, radiation, such as UV radiation (for example solar radiation, which may result in sun-burn), ionizing radiation (for example as a result of cancer treatment or exposure to radioactive nuclear compounds), rough surfaces (which may result in abrasion of the skin), and exposure to substances that are harmful to the skin.

For cosmetic purposes, skin care compositions may also be directed to treat or delay the visible signs of aging of the skin, e.g. by slowing down aging of the skin and/or by rejuvenating the skin, addressing various aspects including, for example, wrinkling of the skin, sagging of the skin, loss of elasticity, age spots, hyperpigmentation and the like. To achieve effective treatment, the type of skin (e.g. dry, oily, sensitive (to e.g. solar radiation or physical contact), dark, light), must be also considered when a specific skin care product is designed. In addition, there is a growing need for hypo-allergenic or even anti-allergenic skin care products.

Wounds are caused by a disruption in the structural integrity of biological tissue. The wound healing and tissue repair is a complex and dynamic process which often is inadequate or unacceptably slow. Wound healing process includes variety of biochemistry events acting in orchestrated cascade to repair the damage. The classic model of wound healing encompasses four sequential, yet overlapping, phases comprising hemostasis, inflammation, proliferation, and remodeling. The events of each phase must occur in a precise and regulated manner. The hemostasis stops the bleeding by generating blood clots. During the inflammation phase, platelet aggregation and clotting form a matrix which traps plasma proteins and blood cells to induce the influx of various types of cells. During the cellular proliferation phase, new connective or granulation tissue and blood vessels are formed. During the remodeling phase, granulation tissue is replaced by a network of collagen and elastin fibers leading to the formation of scar tissue.

Wound healing process can become impaired by patient- or wound type factors. This is especially true in certain chronic diseases such as diabetes in the elderly, and in cancer patients. Treatments of such severe sores may include applying of autologous plasma therapies. For example, platelet rich plasma is utilized for treating hard-to-heal acute and chronic wounds (Lacci et al. 2010. Yale Journal of Biology and Medicine 83:1-9; Carter et al. 2011. Eplasty 11:e38). The combination of variety of cellular and acellular plasma components was found to improve the healing process. However, the use of plasma per se is restricted to an autologous use because of immunological response against foreign antigens and potential harming viruses.

Several isolated plasma proteins such as collagen, fibrin, fibronectin, elastin, and albumin, were shown to assist in the wound healing process.

U.S. Pat. No. 5,641,483 discloses gel and cream formulations comprising human plasma fibronectin for use in promoting wound healing in humans.

U.S. Pat. No. 4,427,651 discloses a sprayable admixture comprising thrombin, stabilizing agent such as albumin, globulin and/or fibrinogen, and a fibrinolysis inhibitor. The sprayable admixture is used for accelerating hemostasis and optimizing biochemical control of wound closure.

U.S. Pat. No. 4,427,650 discloses an enriched plasma derivative for supporting wound closure and healing, containing fibrinogen and a fibrinolysis inhibitor.

U.S. Pat. No. 7,691,816 discloses pharmaceutical compositions comprising TGF-beta superfamily members and sugars for treating wounds and fibrosis.

U.S. Pat. No. 5,631,011 discloses tissue treatment composition comprising fibrin or fibrinogen and biodegradable and biocompatible polymer.

EP Patent No. 1257304 discloses a foam wound dressing, comprising albumin.

U.S. Pat. No. 6,638,909 discloses the use of alpha-1-antitrypsin compositions in wound healing process.

U.S. Pat. No. 7,399,746 discloses pharmaceutical compositions containing fragments of alpha-1 proteinase inhibitor (API) for treating wounds.

U.S. Pat. No. 8,962,813 discloses a process for manufacturing of a composition containing a purified factor for supporting wound healing, typically from blood, the factor being selected from the group consisting of Hepatocyte Growth Factor (HGF), platelet derived growth factor (PDGF), Epidermal growth factor (EGF), transforming growth factor alpha (TGF-α), Transforming growth factor beta (TGF-β), insulin like growth factor (IGF-I) and Fibroblast growth factor (FGF). The manufacturing process comprises purification steps which are performed in the presence of antithrombin III (AT-III).

For the purpose of deriving therapeutic components from blood plasma, a large number of fresh or frozen plasma units are pooled together from various donors. Human plasma proteins for therapeutic use have been manufactured from large pools of plasma for over 50 years. One of the important concerns of single donor or pooled plasma, however, is viral safety. Though every donor who contributes to the pool of plasma is tested individually for viruses, including HIV, HBV, HCV, etc., before blood or plasma donation, there remains a small risk of infection with viruses due to "window period donations," that is donations made between the initial acquisition of infection and the detection of a positive test result with existing diagnostics due to inherent technical limitations. Even a single donor infected with a pathogen, which remained undetected after screening, can potentially contaminate an entire pool of plasma and infect many or all recipients exposed to the pool. Therefore, there is a need to address the viral safety of pooled plasma or the therapeutic proteins derived therefrom.

Although several plasma-derived proteins are known to have wound healing effect, there is a need for additional allogeneic, standardized, hypoallergenic wound healing compositions providing sufficient efficacy together with viral safety and high patient tolerance. Additionally, there is a need for innovative compositions effective in skin care providing protection to the skin and improving its appearance.

SUMMARY OF THE INVENTION

The present invention provides protein compositions derived from Cohn fraction IV and/or Cohn fraction IV-1 from which the majority of AAT has been removed, resulting in protein compositions enriched with, among others, transferrin, immunoglobulins, and haptoglobin and have reduced content of AAT as compared to the source Cohn fraction IV and or fraction IV-1. The compositions of the invention are useful in skin care, including for therapeutic use in promoting wound healing and for cosmetic use for improving skin health and appearance. The protein compositions of the present invention are a by-product of the industry of plasma-derived active substances utilizing Cohn fraction IV and/or VI-1 and thus not only the cosmetic and therapeutic compositions produced are efficacious, they have high economic value.

The present invention is based in part on the unexpected discovery that protein fractions obtained from Cohn fraction IV and/or IV-1 paste after AAT is removed for further processing show a dramatic effect on wound healing. Moreover, the inventors of the present invention show, surprisingly, that the protein combination of the composition of the present invention was more effective in improving wound healing compared to a composition comprising highly purified AAT.

Without wishing to be bound by any particular theory or mechanism of action, the wound healing activity and the improvement of skin health and appearance may be attributed to the unique combination of plasma proteins and other compounds resulting from the process of AAT removal. In addition, the small amount of AAT residing in the composition may shift the balance of protease/anti-protease activity to the favor of proteases, enabling removal of deleterious proteins and contributing to the wound healing process and preventing the formation of excess scar tissue.

Overall, the teachings of the present invention are advantageous over previously known compositions in that present compositions show a synergetic effect, are safe for use and are manufactured using by-products that are otherwise wasted, at a relatively low cost. In recent decades, the skin care industry presented a variety of synthetic proteins to the marketplace, mainly for anti-aging products. However, human-derived proteins bring yet a new level of opportunity and premise being innate to the body with known functions and safety measures.

According to one aspect, the present invention provides a composition comprising a combination of proteins derived from Cohn fraction IV and/or IV-1 paste, wherein the composition is enriched with at least one of transferrin, immunoglobulin, haptoglobin and alpha-2-macroglobulin and comprises reduced content of alpha-1 antitrypsin (AAT).

According to certain embodiments, the percentage of the at least one of transferrin, immunoglobulin, haptoglobin and alpha-2-macroglobulin out of said composition total protein content is elevated compared to the percentage of said proteins out of the total protein content of the Cohn fraction IV and/or Cohn fraction IV-1 paste.

According to certain embodiments, the AAT content is 10% or less out of the total protein content of the composition.

According to certain embodiments, the AAT content is 5% or less, typically 4% or less AAT out of the total protein content of the composition. Each possibility represents a separate embodiment of the present invention. According to certain exemplary embodiments, the AAT content is between about 0.5% to about 5.0% out of the total protein content.

According to certain exemplary embodiments, the composition further comprises at least one additional protein selected from albumin and ceruloplasmin Each possibility represents a separate embodiment of the present invention.

According to some embodiments, the transferrin content is at least 5%, at least 10%, at least 15%, at least 20%, at least 25%, at least 30% m at least 35% m at least 40%, at least 45% or at least 50% out of the total protein content of the composition. Each possibility represents a separate embodiment of the present invention. According to some embodiments, the transferrin content is between 5% and 50% out of the total protein content of the composition. According to some embodiments, the transferrin content is between 10% and 40% out of the total protein content of the composition. According to certain embodiments, the transferrin content is about 35% of the total protein content of the composition.

According to certain embodiments, the immunoglobulin comprises IgA, IgG or a combination thereof. Each possibility represents a separate embodiment of the present invention.

According to some embodiments, the IgA content is at least 5%, at least 7%, at least 9%, at least 11% at least 13% or at least 15% out of the total protein content of the composition. Each possibility represents a separate embodiment of the present invention. According to some embodiments, the IgA content is between 5% and 15% out of the total protein content of the composition. According to some embodiments, the IgA content is between 10% and 15% out of the total protein content of the composition. According to certain other embodiments, the IgA content is between 5% and 10% out of the total protein content of the composition.

According to some embodiments, the IgG content is at least 5%, at least 7%, at least 9%, at least 11% at least 13% or at least 15% out of the total protein content of the composition. Each possibility represents a separate embodiment of the present invention. According to some embodiments, the IgG content is between 5% and 15% out of the total protein content of the composition. According to some embodiments, the IgG content is between 10% and 15% out of the total protein content of the composition. According to certain other embodiments, the IgG content is between 5% and 10% of the total protein content of the composition.

According to some embodiments, the alpha 2-macroglobulin content is at least 5%, at least 7%, at least 9%, at least 11% at least 13% or at least 15% out of the total protein content of the composition. Each possibility represents a separate embodiment of the present invention. According to some embodiments, the Alpha 2-macroglobulin content is between 5% and 15% out of the total protein content of the composition. According to some embodiments, the Alpha 2-macroglobulin content is between 7% and 13% out of the total protein content of the composition.

According to some embodiments, the haptoglobin content is at least 1%, at least 3%, at least 5%, at least 7%, at least 9%, at least 11% at least 13% or at least 15% out of the total protein content of the composition. Each possibility represents a separate embodiment of the present invention. According to some embodiments, the haptoglobin content is between 1% and 15% out of the total protein content of the composition. According to some embodiments, the haptoglobin content is between 5% and 10% out of the total protein content of the composition.

According to some embodiments, the ceruloplasmin content is at least 1%, at least 3%, at least 5%, at least 7%, at least 9%, or at least 10% out of the total protein content of the composition. Each possibility represents a separate embodiment of the present invention. According to some embodiments, the ceruloplasmin content is between 1% and 10% out of the total protein content of the composition. According to some embodiments, the ceruloplasmin content is between 3% and 7% out of the total protein content of the composition.

According to some embodiments, the composition further comprises albumin. According to some embodiments, the albumin content is between 1% and 10% out of the total protein content of the composition. According to some embodiments, the albumin content is between 1% and 5% out of the total protein content of the composition. According to certain embodiments, the Albumin content is about 2% out of the total protein content of the composition.

According to certain exemplary embodiments, the composition of the present invention comprises a combination of proteins derived from Cohn fraction IV and/or Cohn fraction IV-1 paste comprising, out of the total protein content of the composition, 5%-50% transferrin, 5%-20% IgA, 5%-20% IgG, 5%-15% Alpha 2-macroglobulin, 5%-15% haptoglobin, 1%-10% ceruloplasmin and less than 10% AAT.

According to some embodiments, the compositions of the invention are provided in a form suitable for topical application onto the skin. According to certain embodiments, the compositions of the invention comprise a medium (vehicle, diluents or carrier) which is compatible with human skin. These compositions can be, in particular, in the form of aqueous, alcoholic or aqueous/alcoholic solutions, ointments, lotions, gels, water-in-oil or oil-in-water emulsions having the appearance of a cream or a gel, microemulsions or aerosols, cream, foam, lotion, mousse, salve, slurry, spray, paste, suspension, and wound dressing or alternatively in the form of vesicular dispersions containing ionic and/or nonionic lipids. Each possibility represents a separate embodiment of the invention.

According to certain embodiments, the composition is a pharmaceutical composition further comprising a pharmaceutically acceptable diluent or carrier.

According to additional embodiments, the composition is a cosmetic composition further comprising a cosmetically acceptable diluent or carrier.

According to yet additional embodiments, the composition is a dermatology composition further comprising dermatological acceptable diluent or carrier.

According to certain embodiments, the compositions of the invention further contain adjuvants and additives that are common in the corresponding fields, such as hydrophilic or lipophilic gelling agents, preservatives, antioxidants, solvents, fragrances, fillers, UV-screening agents and dyestuffs and colorants. According to additional embodiments, the compositions further comprise hydrophilic or lipophilic active agents.

According to certain embodiments, the compositions of the present invention further comprise added plasma proteins other than the protein derived from the Cohn fraction IV and/or IV-1 including, but not limited to collagen, fibrin, fibronectin, elastin and thrombin.

The pharmaceutical and/or cosmetic composition may, according to some embodiments of the invention, further comprise at least one antibiotic agent. According to certain embodiments, the antibiotic agent is selected from the group consisting of broad-spectrum antibiotics, chlorohexidine, povidone iodine, mafenide acetate, neosporin, metronidazole, polymyxin B sulfate. Each possibility represents a separate embodiment of the invention.

According to some embodiments, the cosmetic and/or the pharmaceutical composition further comprises at least one antiseptic agent. According to certain embodiments, the antiseptic agent is selected from the group consisting of silver sulphadiazine and silver ions compositions. Each possibility represents a separate embodiment of the invention.

According to the embodiments wherein the composition is a pharmaceutical composition, the pharmaceutically acceptable diluent or carrier may be selected from the group consisting of water, organic solvent, inorganic solvent, buffering agent, acidifying agent alkalizing agent and any combination thereof. Each possibility represents a separate embodiment of the invention.

According to other embodiments, the pharmaceutically or cosmetically acceptable diluent or carrier is an ingredient selected from the group consisting of ointment bases, antimicrobial preservative, antioxidant, plasticizer, stiffening agent and any combination thereof. Each possibility represents a separate embodiment of the invention.

According to some embodiments, the pharmaceutical composition further comprises at least one analgesic agent. According to certain embodiments, the analgesic agent is selected from the group consisting of prilocaine, lidocaine, tetracaine, procaine, mepivacaine, benzocaine, bupivacaine and etidocaine. Each possibility represents a separate embodiment of the invention.

According to certain embodiments of the invention, the pharmaceutical or dermatological composition of the inventions is for use in promoting wound healing. According to certain exemplary embodiments, the pharmaceutical or dermatological composition is for reducing scar formation and/or improving scar appearance.

According to another aspect, the present invention provides a method for promoting wound healing, the method comprising topically administering to the skin of a subject in need thereof a pharmaceutical or dermatological composition according to the present invention, thereby promoting wound healing.

According to certain embodiments, the skin of the subject comprises at least one wound. According to certain exemplary embodiments, the composition is applied on or within the wound.

According to certain embodiments, promoting wound healing comprises reducing scar formation and/or improving scar appearance.

According to additional embodiments promoting wound healing comprises at least one outcome selected from the group consisting of infection reduction, infection elimination and epithelialization of the wound area. Each possibility represents a separate embodiment of the present invention.

According to certain exemplary embodiments, promoting wound healing comprises promotion of epithelialization at a higher rate compared to a wound area not treated with the composition.

According to certain embodiments, the pharmaceutical composition is administered onto the wound.

According to some embodiments, the subject is human.

According to some embodiments, the composition for topical administration is in the form selected from the group consisting of solutions, emulsions, foams, lotions, aerosols, bandages, dressing materials, alginate dressing and other wound dressings. Each possibility represents a separate embodiment of the invention.

According to some embodiments, the wound is selected from the group consisting of venous stasis ulcer, arterial ulcer, diabetic ulcer, pressure ulcer, traumatic ulcer, and post-surgical wound. Each possibility represents a separate embodiment of the invention.

According to some embodiments, the wound is selected from the group consisting of laceration, abrasion, contusion, and avulsion. Each possibility represents a separate embodiment of the invention.

According to some embodiments, the wound is a penetrating wound. According to certain embodiments, the penetrating wound is selected from stab, skin cut, and surgical cut. Each possibility represents a separate embodiment of the invention.

According to some embodiments, the wound is further covered with sterile covering means. According to certain embodiments, the covering means is occlusive. According to certain embodiments, the covering means is water-impermeable, capable of retaining an aqueous solution or suspension. According to certain embodiments, the covering means is elastic or pliant.

According to additional aspect, the present invention provides a method for improving the health and/or appearance of human skin, the method comprising topically administering to a skin area in need thereof a cosmetic composition according to the present invention, thereby improving the health and/or appearance of the skin area.

According to certain embodiments, improvement of said skin appearance is selected from the group consisting of: (a) treatment, reduction, and/or prevention of fine lines or wrinkles; (b) reduction of skin pore size; (c) improvement in skin thickness, plumpness, and/or tautness; (d) improvement in skin smoothness, suppleness and/or softness; (e) improvement in skin tone, radiance, and/or clarity; (f) improvement in skin texture and/or promotion of retexturization; (g) improvement in skin barrier repair and/or skin barrier function; (h) improvement in appearance of skin contours; (i) restoration of skin luster and/or brightness; ((j) replenishment of essential nutrients and/or constituents in the skin; (k) improvement in skin moisturizing; (l) increase in skin elasticity and/or resiliency; (m) treatment, reduction, and/or prevention of skin sagging; (n) improvement in skin firmness; (o) improving the appearance of acne scars or marks; (p) improving the appearance of stretch marks; (q) reducing skin gain and/or (r) improvement in the appearance of cellulite. Each possibility represents a separate embodiment of the present invention.

According to certain embodiments, the cosmetic composition is administered in a form selected from the group consisting of solution, ointment, lotion, gel, emulsion, aerosol, cream, foam, lotion, mousse, salves, slurry, spray, paste and suspension. Each possibility represents a separate embodiment of the present invention.

Other objects, features and advantages of the present invention will become clear from the following description and drawings.

DETAILED DESCRIPTION OF THE INVENTION

Figure 1:
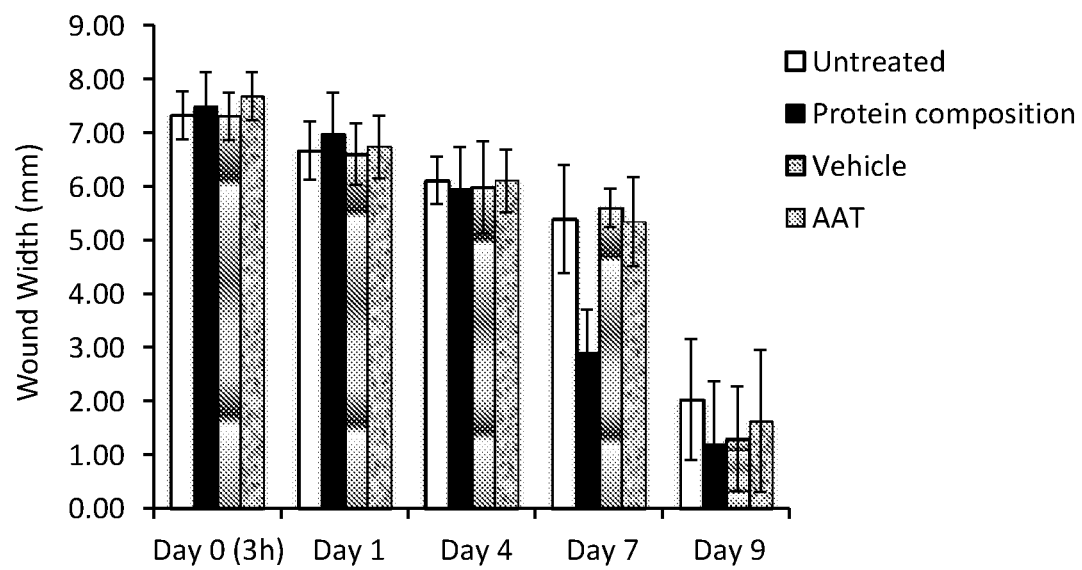
FIG. 1 depicts the wound healing progression in mice, as measured by the wound width at the indicated days following incision.

The present invention provides compositions derived from Cohn Fraction IV and/or IV-1 of human plasma, which are enriched with several proteins while being depleted from others, particularly comprising significantly reduced amounts of AAT compared to the AAT content is the source Cohn fraction material. The compositions of the invention are highly effective in promoting wound healing, particularly in the prevention of scar formation or reducing formation of excess scar tissue and the formation of undesired structures. A significant advantage of the composition of the present invention is that the proteins are human-derived and thus not immunogenic. The compositions of the invention can be also used in cosmetics, being effective in promoting the health and/or the aesthetic appearance of the skin. Advantageously to the use is cosmetics, the compositions comprise mainly compounds having relatively high molecular weight that are not likely to penetrate through healthy intact skin and thus are acceptable for cosmetic use.

The compositions of the invention contain significant amounts of the proteins transferrin, immunoglobulin (IgA and IgG), haptoglobin and alpha-2-macroglobulin that may be promising in therapeutic products for wound healing as well in advanced skin care products such as anti-aging, prebiotics or in inhibition of oxidative stress and inflammation. The protein purification process optimizes and standardizes a composition that is safe, viral free, stable and can be formulated into water-based skin care products.

Definitions

As used herein, the term "promoting wound healing" refers to improving, increasing or inducing closure, healing, or repairs of a wound. Wound healing is considered to be promoted, for example, if the time of healing a wound treated with the pharmaceutical composition of the invention compared to an equivalent wound not treated with the pharmaceutical composition of the invention is decreased by about 10%, or decreased by about 20%, 25%, 30%, 40%, or decreased by about 50%, or decreased by about 75%. Additionally or alternatively, promoting wound healing refers to a decrease in the formation of scar tissue.

As used herein, the term "effective amount" refers to an amount of a composition comprising proteins derived from Cohn fraction paste IV and/or IV-1 according to the teachings of the present invention, which is effective in promoting wound healing or in improving the health and or appearance of human skin as defined hereinabove. According to certain embodiments, the composition is enriched with at least one of transferrin, immunoglobulin, haptoglobin, α-2 macroglobulin or any combination thereof and having reduced content of AAT compared to the Cohn fraction IV or IV-1 source material.

The term "pharmaceutical composition" is intended to be used herein in its broader sense to include preparations containing the composition according to the present invention used for therapeutic purposes. The pharmaceutical composition intended for therapeutic use should contain a therapeutic amount of a composition according to the present invention, i.e., that amount necessary for assisting wound healing and/or reducing scar formation.

The term "dermatological composition" is intended to be used herein in its broader sense to include preparations containing the composition according to the present invention used for promoting healing of flat and/or shallow wounds. The dermatological composition intended for dermatological use should contain a sufficient amount of a composition according to the present invention, i.e., that amount necessary for assisting wound healing and/or reducing scar formation.

The term "cosmetic composition" is intended to be used herein in its broader sense to include preparations containing the composition according to the present invention used for cosmetic purposes. The cosmetic composition intended for cosmetic use should contain an amount of a composition according to the present invention that is effective in improving the health and/or appearance of human skin.

According to one aspect, the present invention provides a composition comprising a combination of proteins derived from Cohn fraction IV and/or IV-1 paste, wherein the composition is enriched with at least one of transferrin, immunoglobulin, haptoglobin and alpha-2-macroglobulin and comprises reduced content of alpha-1 antitrypsin (AAT) compared to the amount of the protein(s) in the Cohn fraction IV and/or IV-1.

According to certain embodiments, the AAT content is 10% or less out of the total protein content of the composition.

According to certain embodiments, the transferrin content within the composition is from about 5% to about 50% out of the total protein content of the composition.

According to certain embodiments, the IgA content within the composition is from about 5% to about 15% out of the total protein content of the composition.

According to certain embodiments, the IgG content within the composition is from about 5% to about 15% out of the total protein content of the composition.

According to certain embodiments, the α2-macroglobulin content within the composition is from about 5% to about 15% out of the total protein content of the composition.

According to certain embodiments, the haptoglobin content within the composition is from about 1% to about 15% out of the total protein content of the composition.

According to certain embodiments, the ceruloplasmin content within the composition is from about 1% to about 10% out of the total protein content of the composition.

According to certain embodiments, the composition further comprises albumin. According to certain exemplary embodiments, the albumin content within the composition is from about 1% to about 10% out of the total protein content of the composition.

According to certain embodiments, the composition further comprises ceruloplasmin. According to certain exemplary embodiments, the ceruloplasmin content within the composition is from about 1% to about 10% out of the total protein content of the composition.

Cohn fraction IV and/or IV-1 paste is produced from blood plasma. The source for the composition of the present invention can be blood plasma or any Cohn fraction as known for a person skilled in the art.

According to certain embodiments, the protein composition of the present invention is purified from Cohn fraction IV and/or IV-1 paste by a process comprising the steps of (a) suspending the Cohn fraction IV and/or IV-1 paste to form a suspension (b) precipitating protein forming a precipitate ("AAT depleted cake"); (c) collecting the precipitate; (d) extracting protein from the precipitate to obtain extracted protein solution; (e) filtering the extracted protein solution to obtain a filtrate; and (f) collecting the filtrate to obtain a protein composition.

According to certain embodiments, the step of precipitating of protein comprises adding to the suspension formed in step (a) polyalkylene glycol. According to certain exemplary embodiments, the polyalkylene glycol is polyethylene glycol. According to additional exemplary embodiments, the polyethylene glycol is added at a concentration of from about 11% to about 15%.

According to certain embodiments, the process further comprises at least one of diafiltration, viral inactivation, viral removal, formulation, lyophilization and any combination thereof. Implementing viral inactivation and/or removal step has significant contribution to the safety of the compositions of the invention in the therapeutic as well as the cosmetic use.

The protein compositions of the invention are odorless. Typically, the compositions are lyophilized composition having the appearance of white powder, which is water soluble and suitable for water-based pharmaceutical and cosmetic products (such as emulsions, lotions, gels and powders).

According to certain exemplary embodiments, the composition of the present invention comprises a combination of proteins derived from Cohn fraction IV and/or Cohn fraction IV-1 paste comprising, out of the total protein content of the composition, 5%-50% transferrin, 5%-20% IgA, 5%-20% IgG, 5%-15% Alpha 2-macroglobulin, 5%-15% haptoglobin, 1%-10% ceruloplasmin and less than 10% AAT.

According to certain exemplary embodiments, the composition of the present invention consists of a combination of proteins derived from Cohn fraction IV and/or Cohn fraction IV-1 paste comprising, out of the total protein content of the composition, 5%-50% transferrin, 5%-20% IgA, 5%-20% IgG, 5%-15% Alpha 2-macroglobulin, 5%-15% haptoglobin, 1%-10% ceruloplasmin and less than 10% AAT.

According to certain exemplary embodiments, the most abundant proteins within the composition of the invention include, but are not limited to, transferrin, immunoglobulins (in particular IgA and IgG); α2-macroglobulin, and haptoglobin.

Transferrin is an iron-binding blood plasma glycoprotein that controls the level of free iron in biological fluids creating an environment low in free iron that impedes bacterial survival in a process called iron withholding. Without wishing to be bound by any specific theory or mechanism of action, the presence of transferrin in the composition may contribute to the antiseptic activity of the composition, by controlling the skin and/or wound microbiota.

Alpha 2-macroglobulin (α2-macroglobulin; A2M) is a serpin protease inhibitor having anti inflammatory properties and immunoglobulins are important factors that neutralize pathogens that control the microbiota of the wound and/or the intact skin.

Haptoglobin is an acute phase protein which can bind free hemoglobin, act as an antioxidant, has antibacterial activity and plays a role in modulating many aspects of the acute phase response. It is thus highly valuable in the composition of the invention. For cosmetic applications, its ant-oxidative properties are of high importance.

According to certain exemplary embodiments, the composition further comprises albumin.

Albumin is carrier of positively charged molecules, and can bind water with the horny layer and annexes of the skin. Its potential activity in skin care includes anti-aging effect by its tightening feeling that appears to smooth wrinkles.

Without wishing to be bound by any specific theory or mechanism of action, the promotion of wound healing and/or improving the health and/or appearance of human skin may be attributed to the specific combination and ratios of the plasma derived protein within the composition of the invention. The natural characteristic of the proteins may also contribute to their effective activity.

Pharmaceutical and cosmetic compositions in accordance with the present invention are particularly suited to administration to the skin, either to wounded or intact skin.

The wound can be an external wound found in any location of a mammal. A wound is a type of physical trauma where the integrity of the skin or tissue is disrupted as a result from i.e. external force, bad health status, aging, and exposure to sunlight, heat or chemical reaction. If the outer layer of a tissue is damaged the wound is considered an open wound.

Open wounds include, for example, incisions (i.e., wounds in which the skin is broken by, for instance, a cutting instrument (e.g., knife, razor, etc.)), lacerations (i.e., wounds in which the skin is typically broken by a dull or blunt instrument), abrasions (e.g., generally a superficial wound in which the topmost layers of the skin are scraped off), puncture wounds (typically caused by an object puncturing the skin, such as nail or needle), penetration wounds (e.g., caused by an object such as a knife), and gunshot wounds.

Closed wounds are typically wounds in which the skin is not broken. Closed wounds include for example contusions (or bruises) caused by a blunt force trauma that damages tissue under the skin, hematomas caused by damage to a blood vessel that in turn causes blood to collect under the skin, crush injury caused by a great or extreme amount of force applied over a long period of time, acute and chronic wounds.

The compositions of the invention contain a standardized combination of proteins at a certain ratio. Some of these proteins function as proteases and growth factors that may assist in improving skin health and appearance. Thus, according to certain embodiments, the compositions of the invention are used as cosmetic composition useful in improving the health and/or appearance of human skin, particularly the skin of at least one of the face, neck, hands and legs. According to certain exemplary embodiments, the cosmetic composition of the invention is for administering to the face skin.

Generally, the improvement in the condition and/or aesthetic appearance is selected from the group consisting of: reducing dermatological signs of chronological aging, photo-aging, hormonal aging, and/or actinic aging; preventing and/or reducing the appearance of lines and/or wrinkles; reducing the noticeability of facial lines and wrinkles, facial wrinkles on the cheeks, forehead, perpendicular wrinkles between the eyes, horizontal wrinkles above the eyes, and around the mouth, marionette lines, and particularly deep wrinkles or creases; preventing, reducing, and/or diminishing the appearance and/or depth of lines and/or wrinkles; improving the appearance of suborbital lines and/or periorbital lines; reducing the appearance of crow's feet; rejuvenating and/or revitalizing skin, particularly aging skin; reducing skin fragility; preventing and/or reversing of loss of glycosaminoglycans and/or collagen; ameliorating the effects of estrogen imbalance; preventing skin atrophy; preventing, reducing, and/or treating hyperpigmentation; minimizing skin discoloration; improving skin tone, radiance, clarity and/or tautness; preventing, reducing, and/or ameliorating skin sagging; improving skin firmness, plumpness, suppleness and/or softness; improving procollagen and/or collagen production; improving skin texture and/or promoting retexturization; improving skin barrier repair and/or function; improving the appearance of skin contours; restoring skin luster and/or brightness; minimizing dermatological signs of fatigue and/or stress; resisting environmental stress; replenishing ingredients in the skin decreased by aging and/or menopause; improving communication among skin cells; increasing cell proliferation and/or multiplication; increasing skin cell metabolism; retarding cellular aging; improving skin moisturizing; enhancing skin thickness; increasing skin elasticity and/or resiliency; enhancing exfoliation; improving microcirculation; decreasing and/or preventing cellulite formation; and any combinations thereof.

According to certain embodiments, the compositions of the invention, either for pharmaceutical use of promoting wound healing or for cosmetic use further comprises at least one antibiotic agent. According to other embodiments, the composition further comprises at least one antiseptic agent.

According to yet another embodiment, the antiseptic agent has at least one of the following antimicrobial activities: antifungal, antibacterial, antiviral and antiprotozoal.

According to yet another embodiment, the at least one antiseptic compound is selected from the group consisting of silver sulphadiazine and silver ions compositions.

The antiseptic composition may further comprise steroidal anti-inflammatory agents (e.g. corticosteroids and synthetic analogs thereof) and antifungal agents such as nystatin and econazole nitrate.

The term "antiseptic" as used herein is in accordance with the meaning normally assigned thereto in the art and further described herein. An antiseptic agent or composition having an antimicrobial activity comprising one or more of the following activities: antifungal activity, antibacterial activity, antiviral activity and/or antiprotozoal activity.

The particular antiseptic and antibiotic agents of the antiseptic composition according to the present invention are selected from those commonly known and available in the medical and cosmetic industries, usually comprising heavy metal ions.

The pharmaceutical compositions of the invention can further comprise other agents, such as anesthetics.

The composition according to the present invention, typically pharmaceutical composition but also the cosmetic compositions may further comprise antiviral agents selected from a wide variety of water-soluble and water-insoluble drugs and their acid addition or metallic salts. Both organic and inorganic salts may be used provided the antiviral agent maintains its medicament value. The antiviral agents may be selected from a wide range of therapeutic agents and mixtures of therapeutic agents which may be administered in sustained release or prolonged action form. Non-limiting illustrative categories of such antiviral agents include RNA synthesis inhibitors, protein synthesis inhibitors, immunostimulating agents, protease inhibitors, and cytokines. Non limiting illustrative specific examples of such antiviral agents include the following medicaments.

(i) Ribavirin (1-β-D-ribofuranosyl-1,2,4-triazole-3-carboxamide, trade name-Virazole™) is an antiviral drug provided as a sterile, lyophilized powder. The empirical formula is $C_8H_{12}N_4O_5$ and the molecular weight is 244.2 Daltons. Ribavirin has antiviral inhibitory activity in vitro against respiratory syncytial virus, influenza virus, and herpes simplex virus. Ribavirin is also active against respiratory syncytial virus (RSV) in experimentally infected cotton rats. In cell cultures, the inhibitory activity of ribavirin for RSV is selective.

(ii) Vidarabine (adenine arabinoside, Ara-A, 9-β-D-arabinofuranosyladenine monohydrate, trade name-ViraA™) is an antiviral drug. Vidarabine is a purine nucleoside obtained from fermentation cultures of *Streptomyces* with the empirical formula, $C_{10}H_{13}N_5O_4.H_2O$. Vidarabine possesses in vitro and in vivo antiviral activity against Herpes simplex virus types 1 and 2 (HSV-1 and HSV-2), and in vitro activity against varicella-zoster virus (VZV). Vidarabine is converted into nucleotides which inhibit viral DNA polymerase.

(iii) Phenol (carbolic acid, $C_6H_6O$) is a topical antiviral, anesthetic, antiseptic, and antipruritic drug.

(iv) Amantadine hydrochloride (1-adamantanamine hydrochloride, trade name-Symmetrel™) has pharmacological actions as both an anti-Parkinson and an antiviral drug. The antiviral activity of amantadine hydrochloride against influenza A appears to be the prevention of the release of infectious viral nucleic acid into the host cell.

According to yet another embodiment, the antibiotic agent is selected from the group consisting of broad-spectrum antibiotics, chlorohexidine, povidone iodine, mafenide acetate, neosporin, metronidazole, chlorine dioxide ($ClO_2$) and polymyxin B sulfate. Each possibility represents a separate embodiment of the present invention.

Known agents that effect wound repair can also be included in the pharmaceutically composition to augment the wound healing process. Such agents include members of the family of growth factors, including, but not limited to, insulin-like growth factor (IGF-1), platelet derived growth factor (PDGF), epidermal growth factor (EGF), transforming growth factor beta (TGF-beta), basic fibroblast growth factor (bFGF), thymosin-alpha1 (T-alpha1) and vascular endothelial growth factor (VEGF).

According certain embodiments, the wound is further covered with sterile covering means. According to another embodiment, the covering means is occlusive. According to an alternative embodiment, the covering means is water-impermeable and is capable of retaining an aqueous solution or suspension. According to certain embodiments, the covering is elastic or pliant.

The terms "occlusive" or "occlusive dressing" are interchangeably used herein to describe dressing that surrounds or covers a damaged area and may also surround or cover healthy tissue in the periphery of the damaged area. This dressing does not allow leakage of material from (such as exudate) or out of the area surrounded or covered by the dressing.

Covering means may be in the form of fibrous nets, fibrous knotted nets, gauze, non-woven cover, sponges or honeycomb absorbent pad, perforated film absorbent dressing, such as Melolin™ (Smith & Nephew Healthcare Ltd.), Telfa™ (The Kendall Company Ltd.) or any other acceptable form and may be made of natural or synthetic, stable or degradable or biodegradable material, as those described in "Remington's Pharmaceutical Sciences", Mack Publishing Company, 1990, pages 1895-1900 or other similar source manuscripts.

The covering means may be water-impermeable thereby rendering it capable of retaining an aqueous solution or suspension. Additionally the covering may be elastic or pliant so as to accommodate itself to the contours of the organ that includes the damaged tissue.

The selection of the cover dressing is governed by the condition of the wound. If significant quantities of exudate are anticipated, a simple absorbent pad may be used, held in position with tape or a bandage, as appropriate. On lightly exuding wounds, a less permeable secondary dressing may be required, such as a perforated film absorbent dressing (Melolin or Telfa, for example). If the wound is very dry, a more occlusive covering may be used to reduce water vapor loss and to prevent the dressing drying out; a film dressing such as Opsite Flexigrid is suitable for this purpose. In the management of difficult wounds such as the hand or foot, the dressing may be retained on the wound in a suitably shaped plastic bag, forming a simple glove or boot.

Application or administration of compounds and/or compositions effective in wound healing may need to be repeated. According to certain embodiments, 1 to 20 treatments are applied, typically from 5 to 10 treatments may be needed to promote wound healing.

According to certain embodiments, the pharmaceutical composition is applied to the wound about every 6 to about every 72 hours.

For cosmetic use, the amount of the protein composition within the cosmetic preparation depends on the route of administration, the phenomenon to be treated and on parameters related to the user including age, gender and application regime.

According to certain exemplary embodiments, the cosmetic composition comprises 1% of the protein composition of the invention. According to these embodiments, the cosmetic composition is applied twice daily. According to certain embodiments, the composition is applied to intact skin. According to additional exemplary embodiments, the cosmetic composition is applied onto the skin of the face.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

Example 1: Preparation of the Protein Composition

A. Preparation of the Protein-Comprising Composition from Cohn Fraction IV

Cohn Fraction IV, batch no. 87AB03612 manufactured with Harbolite 900 filter-aid by Biotest was used as starting material. Fraction IV paste (85.3 g) was added to 432 ml water followed by pH adjustment to 9.4±0.1 with 0.5 M NaOH. Aerosil (49-56 g/kg Fraction IV paste) was added to the suspension with mixing. The pH of the solution was re-adjusted to 9.3-9.5 with 0.5 M NaOH. The suspension temperature was raised to 34±1 (° C.) for 85-95 minutes. Subsequently, the suspension was cooled down to 25° C. and the pH was adjusted to 6.0-6.2. PEG was added to a final concentration of 0.114-0.120 kg PEG/kg slurry. Following incubation with PEG, the suspension pH was adjusted to 5.7 with 2% acetic acid. The conductivity of the suspension was adjusted to 2.9-3.4 mS/cm with solid NaCl. The final pH of the suspension is expected to be in the range of 5.0-6.0. Filter aid and debris were removed using Buchner funnel. The filtrated material was re-circulated until it became clear. The accumulated cake was washed with acetate buffer containing PEG (concentration as described hereinabove), ethanol and NaCl. This step was ended by additional washing step with same buffer. The cake at this step contains minor amounts of AAT.

The cake was re-suspended with 100 ml of phosphate buffer, filtered through Buchner funnel and washed with additional 100 ml phosphate buffer. The filtrated material (named Fraction A) contains large amount of proteins and shoed significant reduction in the content of AAT. The protein content of main proteins in Fraction A is presented in Table 1.

(without PEG), pH 5.7 and conductivity of 16 mS/cm (Buffer A), filtered through Buchner funnel and washed with additional 100 ml of Buffer A. Then, the protein containing filtrate was further filtered through 'extra thick glass fiber filter' and by 1.2 μm filter. Finally, the protein composition was filtered through sterile 0.2 μm filter to obtain the product protein composition.

Table 2 summarizes the content of main proteins of the composition prepared starting with Cohn fraction IV-I in comparison to their content in the source Cohn fraction IV-1 as are known in the art (percentage of total protein).

TABLE 2

Content of main proteins in the product composition compared to Cohn fraction IV-I

| | % of total protein | | |
|---|---|---|---|
| Protein | Cohn Fraction IV-1 | Product Protein Composition | Enrichment factor |
| IgA | 8.8 | 13.3 | 1.5 |
| IgG | 8.3 | 11.7 | 1.41 |
| Transferrin | 7.3 | 11.0 | 1.51 |
| Alpha 2-macroglobulin | 7.6 | 9.7 | 1.28 |
| Ceruloplasmin | 3.3 | 4.2 | 1.27 |
| AAT | 20 | 4.2 | 0.21 |
| Haptoglobin | 2.5 | 3.9 | 1.56 |
| Albumin | 22.7 | 2.1 | 0.09 |

As is clearly demonstrated in Table 2, the ratio of the product composition protein content to Cohn fraction IV-1 protein content of several proteins is higher than 1.0, representing enrichment of these proteins in the composition of the invention. The compositions of the present are thus

TABLE 1

Content of main proteins in the product composition

| Apolipoprotein (g/L) | Ceruloplasmin (g/L) | AAT (g/L) | Transferrin (g/L) | IgA (g/L) | IgG (g/L) | Haptoglobin (g/L) | Albumin (g/L) |
|---|---|---|---|---|---|---|---|
| 0.054 | 0.1 | 0.26 | 1.75 | 0.3 | 0.27 | 0.49 | 0.501 |
| 1% | 2% | 5% | 34% | 6% | 5% | 9% | 10% |

B. Preparation of the Protein-Comprising Composition from Cohn Fraction IV-1

Cohn Fraction IV-I, a typical batch manufactured with Celpure C300 filter-aid by Baxter was used as starting material. Fraction IV-I paste (285-315 kg) was added to 1700 Liter water followed by pH adjustment to 9.2±0.1 with 0.5 M NaOH. Aerosil (28-32 g/kg Fraction IV-I) was added to the suspension with mixing. The pH of the solution was re-adjusted to 8.6-9.0 with 0.5 M NaOH. The suspension temperature was raised to 38±1 (° C.) for 85-95 minutes. Subsequently, the suspension was cooled down to 25° C. and the pH was adjusted to 5.8-6.0. PEG was added to a final concentration of 0.13 kg PEG/kg slurry. Following incubation with PEG, the suspension pH was adjusted to 5.9 with 2% acetic acid. The conductivity of the suspension was adjusted to 2.9-3.4 mS/cm with solid NaCl. Filter aid and debris were removed using Filter press. The filtrated material was re-circulated until it became clear (named Fraction A1). The accumulated cake was washed with acetate buffer, pH 5.9, containing PEG (concentration as described hereinabove), ethanol and NaCl (Conductivity 3.0-3.4 mS/cm).

50 g from the Filter Press precipitates were separated and re-suspended in 100 ml sodium-acetate buffer with NaCl significantly different from Cohn Fraction IV-1 in the protein composition, amounts, and ratio between the proteins. On the other hand, AAT and albumin ratios are below 1.0 and represent depletion of these proteins from the composition of the invention compared to Cohn fraction IV-1.

DEAE Sepharose Chromatography:

Optionally, a step for removing PEG 4000 and further removal of AAT was added. A DEAE Sepharose column of 1.6 cm diameter (2.0 cm$^2$ area) was used. The column was packed to a height of 15 cm. Fraction A1 was loaded onto the column. The column was washed with 1.5 column volume (cv) with sodium acetate buffer having pH 6 and conductivity of 1 mS×cm$^{-1}$ (washing buffer A) and about 6 cv of sodium acetate buffer having pH 6 and conductivity of 2 mS×cm$^{-1}$ (washing buffer B). The washed fractions were collected (=washed fractions).

AAT (which was adsorbed to the column) was eluted with appropriate buffers and kept for other purposes. The remaining protein fractions adsorbed to the column were further eluted from the column (eluted fraction). The eluted fraction was combined with the washed fraction, dialyzed against phosphate buffer, sterile filtered, and kept in 1 ml vials.

Example 2: Effect of the Protein Composition on Wound Healing in Mice

The effect of the protein composition of the invention produced as described in Example 1B (including DEAE Sepharose chromatography) on wound healing was examined. The model used was full thickness skin wounds induced in mice.

Study Design and Conditions

Following anesthesia, 2 cm full skin incision wound was performed along the spine in the upper back of all animals. The closure of the incision was monitored periodically by measuring the wound width without scab (not being covered by newly formed epidermis) at the widest area (middle of the wound), using caliper, on study days 1, 4, 7, 9, 12, 14, 16, 20, 25 and 30.

Individual body weights were determined shortly before wound incision on study day 0. These weights were used as baseline measurements. Thereafter, weight was measured at days 1, 4, 7, 9, 12, 14, 16, 20, 25 and 30 after wound incision. The study terminated at day 30.

Three animals (Groups 2-3) or four animals (Groups 4-5) were culled at each time point on study days 2, 5, 10 and 30 for histology assessment. The entire wound area was harvested and stored in 4% formalin for Hematoxylin & Eosin (H&E) staining and histology analysis.

Study Design

The test compounds were administered in a blinded manner (*) as is described in Table 3 below.

TABLE 3 study design-mice

| Group Number | Group size | Treatment | Route | Volume | Dosing Regimen |
|---|---|---|---|---|---|
| 1 | N = 3 | Naïve | N/A | N/A | N/A |
| 2 | N = 12 | Untreated | N/A | N/A | N/A |
| 4* | N = 16 | Vehicle-PBS | Topically | 100 µl | Once a day on top of the wound from study day 0 until study day 29 |
| 3* | N = 12 | Protein composition of the invention (9.6 mg/ml protein from which 1.5 mg/ml is AAT) | Topically | 100 µl | Once a day on top of the wound from study day 0 until study day 29 |
| 5* | N = 16 | AAT 0.2% (2 mg/ml) | Topically | 100 µl | Once a day on top of the wound from study day 0 until study day 29 |

The results are presented in FIG. 1. The data are presented as means±Std. Dev. To determine statistical significance difference, the treatment group is compared to untreated group using one-way ANOVA followed by Tukey post-test (GraphPad).

A p value <0.05 is considered to represent a significant difference.

Body weights were measured, averaged per treatment and treatment day after wound incision and the averages weight percentages were determined and statistically analyzed for differences. No differences were determined between the treatments (data not shown).

Untreated animals (Group 1) exhibited complete wound closure 14 days post incision. These results are in accordance with data presented by Braiman-Wiksman et al., (2007. Toxicologic Pathology. 35:767-779).

No effect was observed on wound closure following topical treatment with PBS (Group 2). Daily topical treatment with the protein composition of the invention (Group 3) resulted in significant reduction in wound width (without scab) on study day 7 suggesting a faster wound closure process: 2.90±0.33 mm vs. 5.60±0.13 mm for the vehicle group (p<0.05) (FIG. 1).

The beneficial effect of the protein composition of the invention was no longer observed in the late phase of wound healing. In this experiment using mice as the model animals, since the test composition was derived from human source, it might induce immunogenic response following daily application, resulting in inhibition and worsening of the wound healing process.

In view of the findings obtained under the conditions of this study, it can be concluded that the protein composition of the invention has activity in increasing wound healing at least at the initial phase of the wound healing process.

Example 3: Effect of AAT Depleted Composition on Wound Healing in Swine

The effect of the protein composition of the invention produced as described in Example 1B hereinabove on wound healing was examined. The model used was full thickness skin wounds induced in domestic swine.

Study Design and Conditions

Figure 2:
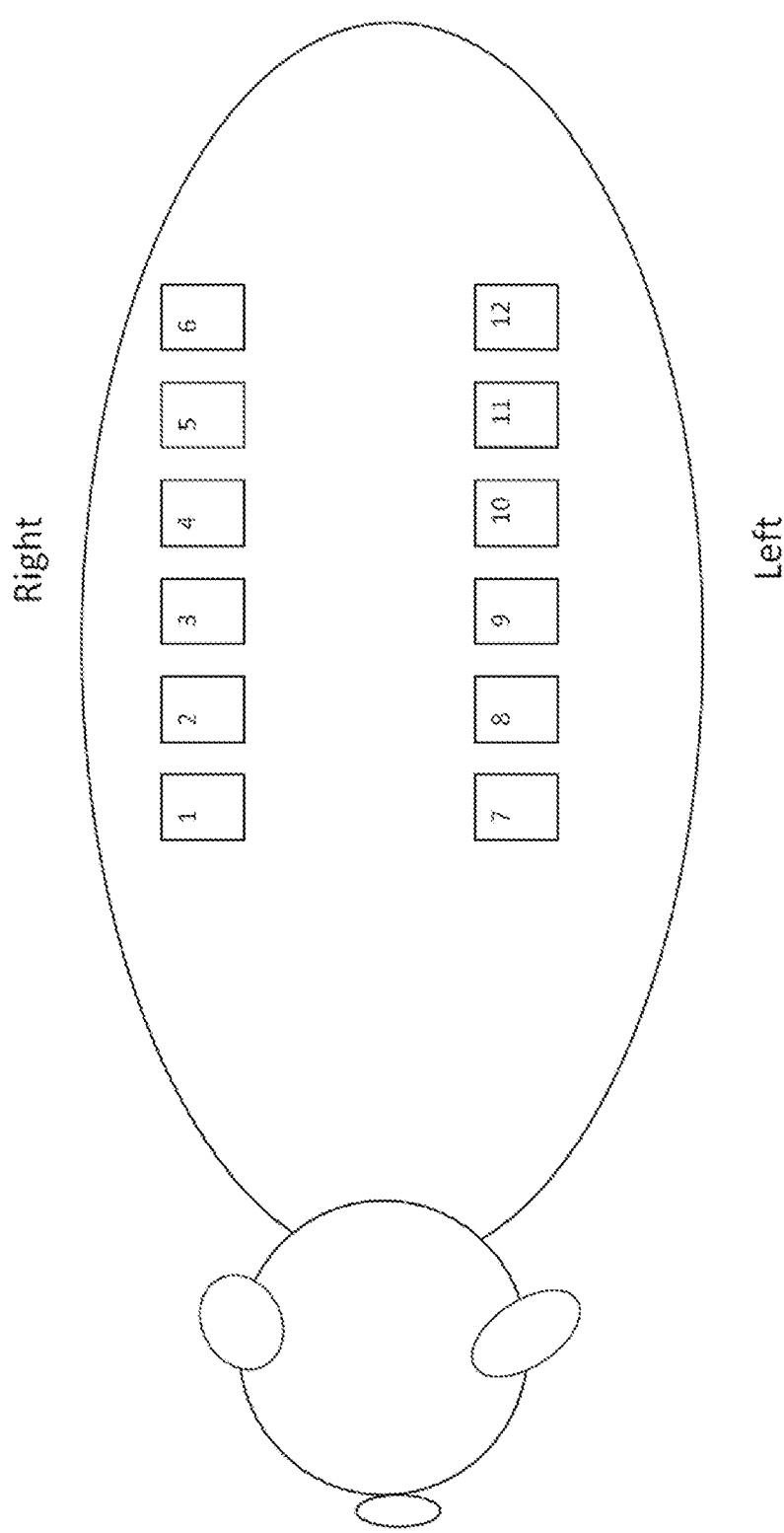
FIG. 2 is a schematic presentation of the full thickness skin wound formed on each test animal.

Following proper sedation and anesthesia, a total of 12 full thickness skin wounds, measuring 2×2 cm, localized bilaterally along the animal's dorsal midline (schematically presented in FIG. 2) were created in 2 animals. Each animal was subjected to a different Test material which was applied topically twice daily for a duration of 14 days post-wounding. Following sacrifice, all Test Sites were excised for histopathological evaluation. The study design is shown in Table 4 hereinbelow.

TABLE 4

Study design-swine

| Animal No. | Model induction | Treatment | | | |
|---|---|---|---|---|---|
| | | Test Materials | Dose | Frequency and duration | Sacrifice time-point |
| 1234 | Creation of 12 full thickness skin wounds 2 × 2 cm on either side of the dorsum | Treatment 2 Formulation #2: Formulation Buffer | 1 ml per Test Site | Twice daily for a duration of 13 days post-wounding | 16 days post-wounding |
| 1251 | | Treatment 1 Formulation #1: protein composition of the invention | | | |

Materials and Methods

Biopsy Collection:

Animals were subjected to sedation and euthanasia according to the Test Facility's standard operating procedures. The wound sites were fully excised by surgical excision with a scalpel blade. The wounds were excised so that healthy skin surrounding the wound on all sides was included. Care was taken to excise the full thickness of the skin.

Immediately following their excision, individual biopsy samples were immediately fixed and preserved in uniquely marked vials containing 10% neutral buffered formalin (approx. 4% formaldehyde solution).

Slides Preparation & Histopathological Examinations:

The harvested biopsies from each animal were transferred to Patho-Lab Diagnostics Ltd. for preparation of slides. Each vial, containing the harvested tissues, was identified by the animal number and Test Site number.

Tissues were trimmed at the middle of the Test Site width, extending from healthy tissue surrounding the site into at least half the length of the site, embedded in paraffin, sectioned at approximately 5 µm, and stained with Hematoxylin & Eosin (H&E).

Following completion of slides preparation, the slides were ready for histopathological evaluation.

Morphometric Evaluation:

Imaging system used: Olympus BX51 microscope equipped with XYZ computer controlled auto stage, & "Retiga-2000R" camera (1600×1200 pixels & RGB revolving filter). Software—"Image Pro Plus" Ver 7.0 AMD (MediaCY, US), Image analysis program & "Stage Pro" for microscope stage XY and focus Z control.

Each slide was scanned by using an objective X10, thus allowing a very good resolution for each field. A binning method of 2 pixels was used in capturing of each image in order to get better sensitivity, better signal to noise ratio and smaller final image volume.

Most of the slide relevant area was scanned microscopically by adding multiple fields to include the entire lesion area+the lesion's margins. The final image was constructed from a total of approximately 100 to 200 fields that covered all the areas of interests in the tissue, thus creating very large and high resolution scanned image.

Figure 3A:
FIG. 3 shows examples of harvested biopsy stained with Hematoxylin and Eosin (HE) (FIG. 3A) and with Masson's Trichrome staining (MT) (FIG. 3B).
Figure 3B:
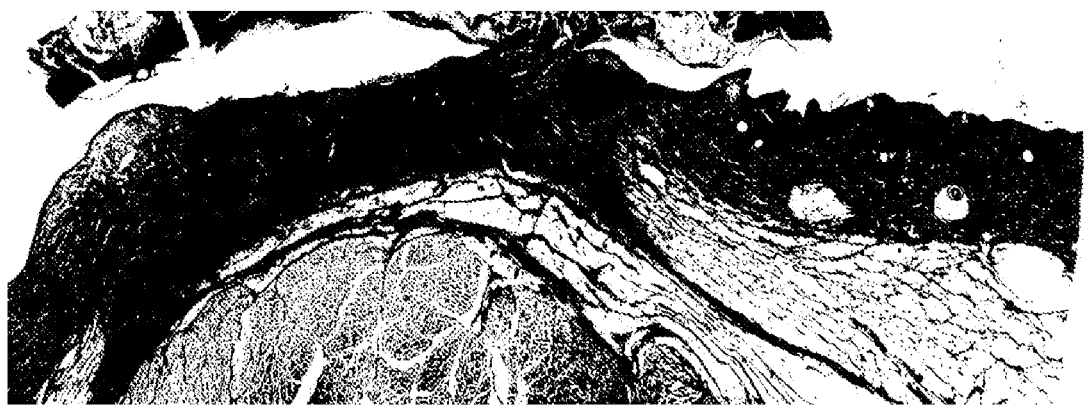

Measurements of lesion's length was done by using the manual tool of length, judging the correct area of lesion by correlating each two full resolution images of the relevant stained tissue, (Heoxiphilin Eosin-H&E & Masson's Trichrome-MT) (FIG. 3).

Figure 4:
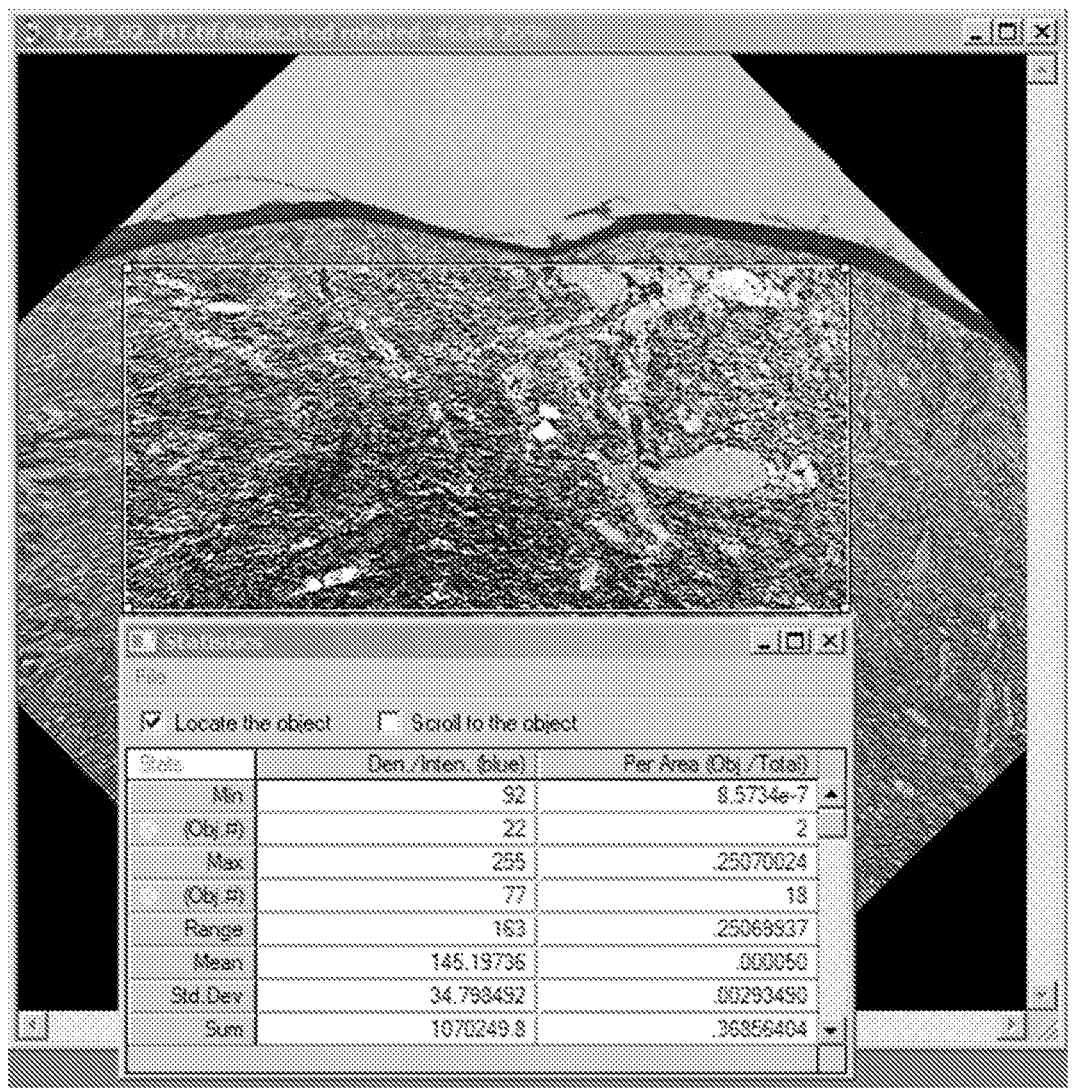
FIG. 4 demonstrates an exemplary measurement of collagen intensity and collagen density.

Density of granulation was always measured inside the same size rectangular Area of Interest (AOI), that was located at each relevant lesion area and the lesion's margins (FIG. 4). In each location two parameters were measured, the relative intensity of the blue stain (Den./Inten. (blue)= collagen intensity, i.e. the levels of blue staining expressed in units between 0 and 255, 0=maximum blue stain/darkest, 255=no blue stain/lightest+the standard deviation of these intensities (STD). (A smaller each Den./Inten number means a darker blue stain). The collagen density equals to the Area fraction occupied by the blue stain (collagen), divided by the constant rectangular area (Per Area). This parameter is expressed in a number between 0 and 1.

Data Evaluation

Histopathological wound assessment was performed in a blinded manner, so that the Veterinary Pathologist was not aware of the treatment identity of different animals at the time of assessment.

The degree of healing was assessed according to the scoring scheme presented in Table 5.

TABLE 5

| | Scoring scheme | | | |
|---|---|---|---|---|
| Score | Degree of wound epithelialization | Dermal Inflammatory cell infiltrate | Crust formation (i.e., dried exudate overlying the epidermis) | Granulation tissue in the dermis |
| 0 | No epithelialization evident | Absent | Absent | Absent |
| 1 | Minimal degree of epithelialization | Minimal | Minimal | Minimal |
| 2 | Mild degree of epithelialization | Mild | Mild | Mild |
| 3 | Moderate/extensive degree of epithelialization | Moderate | Moderate | Moderate |
| 4 | Complete epithelialization | Marked | Marked | Marked |

Any additional parameters deemed relevant by the Veterinary Pathologist were assessed and recorded in addition to the parameters detailed above. Representative micrographs were taken by the pathologist Results Morphogenesis analyses were performed on data obtained from wound sites where no unrelated complications of wound infection and/or inflammation were observed.

Figure 5:
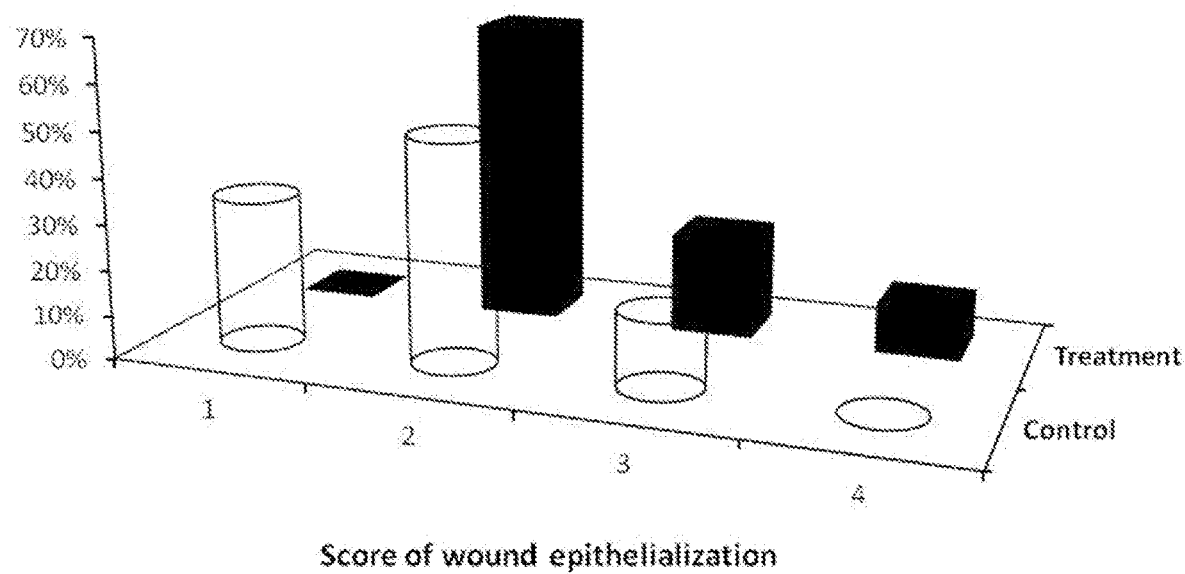
FIG. 5 shows the degree (percentage) of wound epithelialization of wound sites of swine treated with the composition of the invention or not treated, 16 days after incision.

Examining the effects of the test materials on full thickness skin wounds induced in domestic swine, suggests that the test compound (treatment 1, formulation #1) showed a trend of positive effect on accelerating the closure of the induced epithelial wound (incision), when comparing to the untreated group. The animal treated with the protein composition had 0/9 site with no or minimal epithelialization while the vehicle treated animals had 2/6 sites with minimal epithelialization. On the other hand, the animal treated with the protein composition had 1/9 site with complete epithelialization while the vehicle treated animal had 0/6 (FIG. 5; Epithelialization scores as presented in Table 5).

Figure 6:
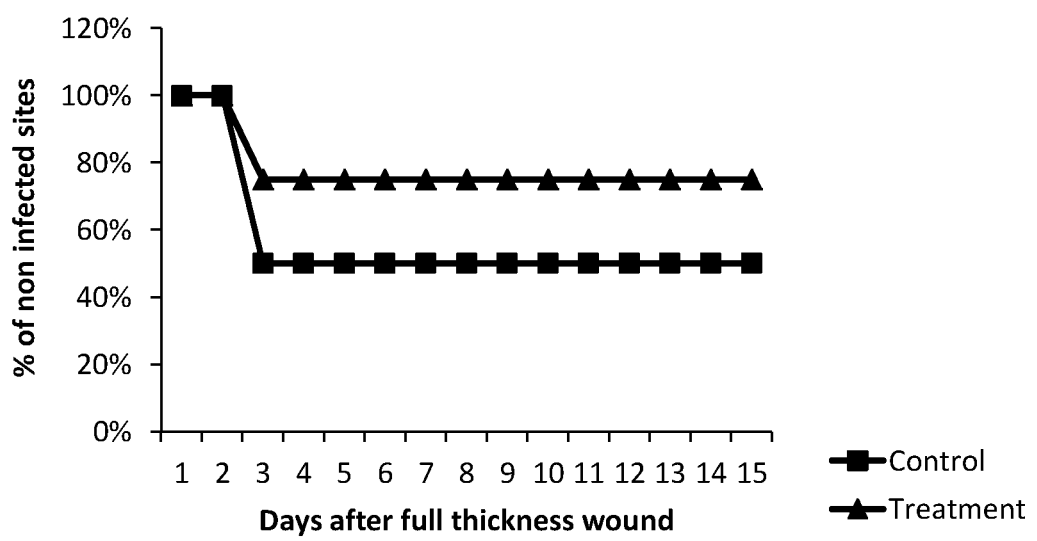
FIG. 6 demonstrated the degree of infection of treated and non treated wound sites of swine up to 15 days after incision.

Moreover, the protein composition inhibited the tendency of the wound to become infected: on day three the animal treated with the protein composition had 3/12 infected sites while the vehicle treated had 6/12 infected wound sites (FIG. 6).

Analysis of the data obtained from morphometric evaluation of the collagen density (i.e., applied on Masson's Trichrome stained sections), both in the areas covered (i.e., healed area) and uncovered by newly formed epithelium, indicated that the protein composition of the invention induced a statistically significant reduction in the density of the collagen present in the scar tissue (i.e., granulation tissue), when comparing to sites that were not treated with the test compound (Table 6). These findings suggest that use of the protein composition of the invention on full thickness skin wounds induced in domestic swine may improve the quality of wound healing and reduce pathological scarring.

TABLE 6

| Collagen density and intensity - statistical analysis | | |
|---|---|---|
| Parameter | P value (Mann-Whitney 2-tailed) Without wound site 3 | P value (Mann-Whitney 2-tailed) With wound site 3 |
| Wound length | 0.797 | 0.864 |
| Collagen Intensity wound center | 0.518 | 0.607 |
| wound margin | 0.797 | 0.864 |

TABLE 6-continued

Collagen density and intensity - statistical analysis

| Parameter | | P value (Mann-Whitney 2-tailed) Without wound site 3 | P value (Mann-Whitney 2-tailed) With wound site 3 |
|---|---|---|---|
| Collagen Density | wound center | 0.042 | 0.026 |
| | wound margin | 0.004 | 0.003 |

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method of promoting wound healing in a subject in need thereof, the method comprising topically administering to the skin of the subject a pharmaceutical composition comprising: (a) proteins derived from at least one of a Cohn fraction IV and Cohn fraction IV-1 paste; and, (b) a pharmaceutically acceptable diluent or carrier; wherein the pharmaceutical composition 0.5-5% alpha-1 antitrypsin (AAT), 1%-15% haptoglobin, 1%-10% ceruloplasmin, 1%-10% albumin, and, 5%-50% transferrin, each as measured by total protein content.

2. The method of claim 1, wherein the wound is selected from the group consisting of a venous stasis ulcer, an arterial ulcer, a diabetic ulcer, a pressure ulcer, a traumatic ulcer, and a post-surgical wound.

3. The method of claim 1, wherein the pharmaceutically acceptable diluent or carrier is dermatologically acceptable.

4. The method of claim 1, wherein the pharmaceutical composition is in a form suitable for topical application onto the skin.

5. The method of claim 4, wherein the form of the pharmaceutical composition is selected from the group consisting of a solution, gel, cream, emulsion, foam, lotion, mousse, salve, slurry, spray, paste, suspension, ointment, and wound dressing.

6. The method of claim 1, wherein the amount of the at least one protein selected from the group consisting of transferrin, immunoglobulin, haptoglobin and alpha-2-macroglobulin in the pharmaceutical composition, as measured by the total protein content, is elevated compared to the amount of the at least one protein in the at least one of the Cohn fraction IV and Cohn fraction IV-i paste.

7. The method of claim 1, wherein the pharmaceutical composition comprises 5%-20% IgA, as measured by total protein content.

8. The method of claim 1, wherein the pharmaceutical composition comprises 5%-20% IgG, as measured by total protein content.

9. The method of claim 1, wherein the pharmaceutical composition comprises 5%-15% Alpha 2-macroglobulin, as measured by total protein content.

10. The method of claim 1, wherein the proteins in the pharmaceutical composition are purified from the at least one of a Cohn fraction IV and Cohn fraction IV-1 by a process comprising the steps of (a) suspending a Cohn fraction IV or Cohn fraction IV-1 paste in an aqueous medium forming a suspension; (b) precipitating proteins from the suspension forming a precipitate; (c) collecting the precipitate; (d) extracting proteins from the precipitate to obtain extracted protein solution; (e) filtering the extracted protein solution to obtain a filtrate; and, (f) collecting the filtrate.

* * * * *